United States Patent [19]

McSwiggen

[11] Patent Number: 5,525,468
[45] Date of Patent: Jun. 11, 1996

[54] ASSAY FOR RIBOZYME TARGET SITE

[75] Inventor: James A. McSwiggen, Solon, Ohio

[73] Assignee: Ribozyme Pharmaceuticals, Inc., Cleveland, Ohio

[21] Appl. No.: 284,746

[22] Filed: Aug. 1, 1994

Related U.S. Application Data

[63] Continuation of Ser. No. 883,849, May 14, 1992, abandoned.

[51] Int. Cl.$^6$ .................................. C12Q 1/68
[52] U.S. Cl. .................... 435/6; 435/91.2; 536/25.1
[58] Field of Search ................ 435/6, 91.2, 91.31; 536/25.1

[56] References Cited

FOREIGN PATENT DOCUMENTS 9115580 10/1991 WIPO.

OTHER PUBLICATIONS

Lingelbach et al., Nucleic Acids Res, vol. 16, No. 8, pp. 340514 3414, Apr. 25, 1988.
Hampel et al., Nucleic Acids Res, vol. 18, No. 2, pp. 299–304, (1990).
Cech, 260 Jrnl. of Amer. Med. Assoc., "Ribozymes and Their medical Implications" 3031, 1988.
Hsieh et al., In Antiviral Development and the Detection of Virus Infection, published Aug. 1992 by Plenum Press (New York, New York), pp.125–128.
Weizsacker et al., 189 Biochem. and Biophy. Res. Comm., "Cleavage of Hepatitis B Virus RNA by Three Ribozymes Transcribed From a Single DNA Template", 743, 1992.
Sarver et al., 247 Science "Ribozymes as Potential Anti--HIV–1 Therapeutic Agents" 1222, 1990.
Zaia et al., 660 Annals of the New York Academy of Science, "Status of Ribozyme and antisense–Based Developmental Approaches for Anti–HIV–1 Therapy," 95 1992.
Lorentzen et al., 5 Virus Genes, "In Vitro Cleavage of HIV–1 vif RNA by a Synthetic Ribozyme", 17, 1991.

Xing et al., 66 Jrnl. of Virol., "Ribozymes Which Cleave Areanvirus RNAs: Identification of Susceptible Target Sites and Inhibition by Target Site Secondary Structure" 1361, 1992.
Taylor, et al., "Ribozyme–Mediated Cleavage of an HIV–1 gag RNA: The Effects of Nontargeted Sequences and Secondary Structure on Ribozyme Cleavage Activity", 1 Antisense Res and Dev 173, 1991.
Sambrook, et al., "Molecular Cloning: A Laboratory Manual", published by Cold Spring Habor Laboratory Press (N. Y.), pp. 7.71–7.78, 1989.
Scanlon et al., "Ribozyme–Mediated Cleavage of c–fos mRNA reduces gene expression of DNA synthesis enzymes and metallohionein", 88 Proc. Natl. Acad. Sci. 10591, 1991.
Usman et al. "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an Escherichia coil Formylmethioine tRNA", 109 Jrnl of Amer. Chem. Society, 7845 1987.
Slim et al., "Configurationally Defined Phosphorothioate––Containing Oligoribonucleotides in the Study of the Mechanism of Cleavage of Hammerhead Ribozymes"19 Nucl Acids Res. 1183, 1991.

(List continued on next page.)

Primary Examiner—Stephanie W. Zitomer
Assistant Examiner—Scott W. Houtteman
Attorney, Agent, or Firm—Lyon & Lyon

[57] ABSTRACT

Method for determining target site accessibility for a ribozyme by providing a DNA oligonucleotide having a nucleotide sequence complementary to the RNA target. The DNA oligonucleotide is contacted with the RNA target in the presence of an agent, such as RNAseH, such that the RNAseH cleaves the RNA target when the DNA and RNA form a duplex. The occurrence of cleavage is detected by any standard methodology. Those DNA oligonucleotides which provide a detectable level of cleavage indicate that the RNA target site is accessible to ribozyme.

15 Claims, 9 Drawing Sheets

TARGET RNA
+DNA OLIGO
+RNAse H

OTHER PUBLICATIONS

Cameron et al., "Specific Gene Expression by Engineered Ribozymes in Monkey Cells", 86 *Proc. Natl. Acad. Sci.* 9139, 1989.

Dropulic, et al., "Functional Characterization of a U5 Ribozyme: Intracellular Suppression of Human Immunodeficiency Virus Type 1 Expression", 66 *Jrnl of Virol.* 1432, 1992.

Tsukiyama–Kohara et al., "Internal Ribosome Entry Site Within Hepatitis C Virus RNA", 66 *Jrnl of Virol.* 1476, 1992.

Hampel et al., "RNA Catalyst for Cleaving Specific RNA Sequence", filed Sep. 20, 1989, which is a Continuation–in–Part of U. S. Serial No. 07/247,100 filed Sep. 20, 1988.

Mamone et al., "Design of Hammerhead Ribozymes Targeted to Sequence in HIV, HSV, and the RAT ANF GENE", Abstract of Keystone, CO (May 27, 1992).

Pavco et al., "Regulation of Self–Splicing Reaction by Antisense RNA", Abstract of Keystone, CO (May 27, 1992).

5,525,468

ASSAY FOR RIBOZYME TARGET SITE

BACKGROUND OF THE INVENTION

This application is a continuation of application Ser. No. 07/883,849, filed May 14, 1992 now abandoned, This invention relates to methods for determining appropriate target sites for ribozymes:

This application relates to that described by McSwiggen, "Assay for Ribozyme Target Site Accessibility" filed on the same day and assigned to the same assignee as the present application, and the whole of which, including drawings, is hereby incorporated by reference herein.

The following is a brief history of the discovery and activity of enzymatic RNA molecules or ribozymes. This history is not meant to be complete but is provided only for understanding of the invention that follows. This summary is not an admission that all of the work described below is prior art to the claimed invention.

Prior to the 1970s it was thought that all genes were direct linear representations of the proteins that they encoded. This simplistic view implied that all genes were like ticker tape messages, with each triplet of DNA "letters" representing one protein "word" in the translation. Protein synthesis occurred by first transcribing a gene from DNA into RNA (letter for letter) and then translating the RNA into protein (three letters at a time). In the mid 1970s it was discovered that some genes were not exact, linear representations of the proteins that they encode. These genes were found to contain interruptions in the coding sequence which were removed from, or "spliced out" of, the RNA before it became translated into protein. These interruptions in the coding sequence were given the name of intervening sequences (or introns) and the process of removing them from the RNA was termed splicing. After the discovery of introns, two questions immediately arose: (i) why are introns present in genes in the first place, and (ii) how do they get removed from the RNA prior to protein synthesis? The first question is still being debated, with no clear answer yet available. The second question, how introns get removed from the RNA, is much better understood after a decade and a half of intense research on this question. At least three different mechanisms have been discovered for removing introns from RNA. Two of these splicing mechanisms involve the binding of multiple protein factors which then act to correctly cut and join the RNA. A third mechanism involves cutting and joining of the RNA by the intron itself, in what was the first discovery of catalytic RNA molecules.

Cech and colleagues were trying to understand how RNA splicing was accomplished in a single-celled pond organism called *Tetrahymena thermophila*. They had chosen *Tetrahymena thermophila* as a matter of convenience, since each individual cell contains over 10,000 copies of one intron-containing gene (the gene for ribosomal RNA). They reasoned that such a large number of intron-containing RNA molecules would require a large amount of (protein) splicing factors to get the introns removed quickly. Their goal was to purify these hypothesized splicing factors and to demonstrate that the purified factors could splice the intron-containing RNA in vitro. Cech rapidly succeeded in getting RNA splicing to work in vitro, but something funny was going on. As expected, splicing occurred when the intron-containing RNA was mixed with protein-containing extracts from Tetrahymena, but splicing also occurred when the protein extracts were left out. Cech proved that the intervening sequence RNA was acting as its own splicing factor to snip itself out of the surrounding RNA. They published this startling discovery in 1982. Continuing studies in the early 1980's served to elucidate the complicated structure of the Tetrahymena intron and to decipher the mechanism by which self-splicing occurs. Many research groups helped to demonstrate that the specific folding of the Tetrahymena intron is critical for bringing together the parts of the RNA that will be cut and spliced. Even after splicing is complete, the released intron maintains its catalytic structure. As a consequence, the released intron is capable of carrying out additional cleavage and splicing reactions on itself (to form intron circles). By 1986, Cech was able to show that a shortened form of the Tetrahymena intron could carry out a variety of cutting and joining reactions on other pieces of RNA. The demonstration proved that the Tetrahymena intron can act as a true enzyme: (i) each intron molecule was able to cut many substrate molecules while the intron molecule remained unchanged, and (ii) reactions were specific for RNA molecules that contained a unique sequence (CUCU) which allowed the intron to recognize and bind the RNA. Zaug and Cech coined the term "ribozyme" to describe any ribonucleic acid molecule that has enzyme-like properties. Also in 1986, Cech showed that the RNA substrate sequence recognized by the Tetrahymena ribozyme could be changed by altering a sequence within the ribozyme itself. This property has led to the development of a number of site-specific ribozymes that have been individually designed to cleave at other RNA sequences. The Tetrahymena intron is the most well-studied of what is now recognized as a large class of introns, Group I introns. The overall folded structure, including several sequence elements, is conserved among the Group I introns, as is the general mechanism of splicing. Like the Tetrahymena intron, some members of this class are catalytic, i.e., the intron itself is capable of the self-splicing reaction. Other Group I introns require additional (protein) factors, presumably to help the intron fold into and/or maintain its active structure. While the Tetrahymena intron is relatively large, (413 nucleotides) a shortened form of at least one other catalytic intron (SunY intron of phage T4, 180 nucleotides) may prove advantageous not only because of its smaller size but because it undergoes self-splicing at an even faster rate than the Tetrahymena intron.

Ribonuclease P (RNAseP) is an enzyme comprised of both RNA and protein components which are responsible for converting precursor tRNA molecules into their final form by trimming extra RNA off one of their ends. RNAseP activity has been found in all organisms tested, but the bacterial enzymes have been the most studied. The function of RNAseP has been studied since the mid-1970s by many labs. In the late 1970s, Sidney Altman and his colleagues showed that the RNA component of RNAseP is essential for its processing activity; however, they also showed that the protein component also was required for processing under their experimental conditions. After Cech's discovery of self-splicing by the Tetrahymena intron, the requirement for both protein and RNA components in RNAseP was reexamined. In 1983, Altman and Pace showed that the RNA was the enzymatic component of the RNAseP complex. This demonstrated that an RNA molecule was capable of acting as a true enzyme, processing numerous tRNA molecules without itself undergoing any change. The folded structure of RNAseP RNA has been determined, and while the sequence is not strictly conserved between RNAs from different organisms, this higher order structure is. It is thought that the protein component of the RNAseP complex may serve to stabilize the folded RNA in vivo. At least one RNA position important both to substrate recognition and to determination of the cleavage site has been identified, however little else is known about the active site. Because tRNA sequence recognition is minimal, it is clear that some aspect(s) of the tRNA structure must also be involved in substrate recognition and cleavage activity. The size of RNAseP RNA (>350 nucleotides), and the complexity of the substrate recognition, may limit the potential for the use of an RNAseP-like RNA in therapeutics. However, the size of RNAseP is being trimmed down (a molecule of only 290 nucleotides functions reasonably well). In addition, substrate recognition has been simplified by the recent discovery that RNAseP RNA can cleave small RNAs lacking the natural tRNA secondary structure if an additional RNA (containing a "guide" sequence and a sequence element naturally present at the end of all tRNAs) is present as well.

Symons and colleagues identified two examples of a self-cleaving RNA that differed from other forms of catalytic RNA already reported. Symons was studying the propagation of the avocado sunblotch viroid (ASV), an RNA virus that infects avocado plants. Symons demonstrated that as little as 55 nucleotides of the ASV RNA was capable of folding in such a way as to cut itself into two pieces. It is thought that in vivo self-cleavage of these RNAs is responsible for cutting the RNA into single genome-length pieces during viral propagation. Symons discovered that variations on the minimal catalytic sequence from ASV could be found in a number of other plant pathogenic RNAs as well. Comparison of these sequences revealed a common structural design consisting of three stems and loops connected by central loop containing many conserved (invariant from one RNA to the next) nucleotides. The predicted secondary structure for this catalytic RNA reminded the researchers of the head of a hammer; thus it was named as such. Uhlenbeck was successful in separating the catalytic region of the ribozyme from that of the substrate. Thus, it became possible to assemble a hammerhead ribozyme from 2 (or 3) small synthetic RNAs. A 19-nucleotide catalytic region and a 24-nucleotide substrate were sufficient to support specific cleavage. The catalytic domain of numerous hammerhead ribozymes have now been studied by both the Uhlenbeck and Symons groups with regard to defining the nucleotides required for specific assembly and catalytic activity and determining the rates of cleavage under various conditions.

Haseloff and Gerlach showed it was possible to divide the domains of the hammerhead ribozyme in a different manner. By doing so, they placed most of the required sequences in the strand that didn't get cut (the ribozyme) and only a required UH where H = C, A, or U in the strand that did get cut (the substrate). This resulted in a catalytic ribozyme that could be designed to cleave any UH RNA sequence embedded within a longer "substrate recognition" sequence. The specific cleavage of a long mRNA, in a predictable manner using several such hammerhead ribozymes, was reported in 1988.

One plant pathogen RNA (from the negative strand of the tobacco ringspot virus) undergoes self-cleavage but cannot be folded into the consensus hammerhead structure described above. Bruening and colleagues have independently identified a 50-nucleotide catalytic domain for this RNA. In 1990, Hampel and Tritz succeeded in dividing the catalytic domain into two parts that could act as substrate and ribozyme in a multiple-turnover, cutting reaction. As with the hammerhead ribozyme, the hairpin catalytic portion contains most of the sequences required for catalytic activity while only a short sequence (GUC in this case) is required in the target. Hampel and Tritz described the folded structure of this RNA as consisting of a single hairpin and coined the term "hairpin" ribozyme (Bruening and colleagues use the term "paper clip" for this ribozme motif). Continuing experiments suggest an increasing number of similarities between the hairpin and hammerhead ribozymes in respect to both binding of target RNA and mechanism of cleavage. At the same time, the minimal size of the hairpin ribozyme is still 50–60% larger than the minimal hammerhead ribozyme.

Hepatitis Delta Virus (HDV) is a virus whose genome consists of single-stranded RNA. A small region (~80 nucleotides) in both the genomic RNA, and in the complementary anti-genomic RNA, is sufficient to support self-cleavage. As the most recently discovered ribozyme, HDV's ability to self-cleave has only been studied for a few years, but is interesting because of its connection to a human disease. In 1991, Been and Perrotta proposed a secondary structure for the HDV RNAs that is conserved between the genomic and anti-genomic RNAs and is necessary for catalytic activity. Separation of the HDV RNA into "ribozyme" and "substrate" portions has recently been achieved by Been, but the rules for targeting different substrate RNAs have not yet been determined fully. Been has also succeeded in reducing the size of the HDV ribozyme to ~60 nucleotides.

The table below lists some of the characteristics of the ribozymes discussed above:

TABLE 1

Characteristics of ribozymes

Group I Introns

Size: ~300 to >1000 nucleotides.

Requires a U in the target sequence immediately 5' of the cleavage site.

Binds 4–6 nucleotides at 5' side of cleavage site.

Over 75 known members of this class. Found in *Tetrahymena thermophila* rRNA, fungal mitochondria, chloroplasts, phage T4, blue-green algae, and others.

RNAseP RNA M1 RNA)

Size: ~290 to 400 nucleotides.

RNA portion of a ribonucleoprotein enzyme. Cleaves tRNA precursors to form mature tRNA.

Roughly 10 known members of this group all are bacterial in origin.

Hammerhead Ribozyme

Size: ~30 to 40 nucleotides.

Requires the target sequence UH immediately 5' of the cleavage site.

Binds a variable number nucleotides on both sides of the cleavage site.

14 known members of this class. Found in a number of plant pathogens (virusoids) that use RNA as the infectious agent. (See FIG. 7)

Hairpin Ribozyme

Size: ~50 nucleotides.

Requires the target sequence GUC immediately 3' of the cleavage site.

Binds 4 nucleotides at 5' side of the cleavage site and a variable number to the 3' side of the cleavage site.

Only 1 known member of this class. Found in one plant pathogen (satellite RNA of the tobacco ringspot virus) which uses RNA as the infectious agent. (See FIG. 8)

Hepatitis Delta Virus (HDV) Ribozyme

Size: ~60 nucleotides (at present).

Cleavage of target RNAs recently demonstrated.

Sequence requirements not fully determined.

Binding sites and structural requirements not fully determined, although no sequences 5' of cleavage site are required.

Only 1 known member of this class. Found in human HDV. (See FIG. 9)

As the term is used in this application, ribozymes are RNA molecules having an enzymatic activity which is able to repeatedly cleave other separate RNA molecules in a nucleotide base sequence specific manner. Such enzymatic RNA molecules can be targeted to virtually any RNA transcript, and efficient cleavage achieved in vitro. Kim et al., 84 Proc. Nat. Acad. of Sci. USA 8788, 1987, Haseloff and Geriach, 334 Nature 585, 1988, Cech, 260 JAMA 3030, 1988, and Jefferies et al., 17 Nucleic Acid Research 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

By the phrase "enzymatic RNA molecule" is meant an RNA molecule which has complementarity in a substrate binding region to a specified gene target, and also has an enzymatic activity which is active to specifically cleave RNA in that target. That is, the enzymatic RNA molecule is able to intermolecularly cleave RNA and thereby inactivate a target RNA molecule. This complementarity functions to allow sufficient hybridization of the enzymatic RNA molecule to the target RNA to allow the cleavage to occur. 100% complementarity is preferred, but complementarity as low as 50–75% may also be useful in this invention.

In preferred embodiments of this invention, the enzymatic RNA molecule is formed in a hammerhead motif, but may also be formed in the motif of a hairpin, hepatitis delta virus, group I intron or RNAseP RNA (in association with an RNA guide sequence). Examples of such hammerhead motifs are described by Rossi et al., 8 AIDS RESEARCH AND HUMAN RETROVIRUSES 183, 1992, of hairpin motifs by Hampel et al., RNA CATALYST FOR CLEAVING SPECIFIC RNA SEQUENCES, filed Sep. 20, 1989, which is a continuation-in-part of U.S. Ser. No. 07/247,100 filed Sep. 20, 1988, Hampel and Tritz, 28 Biochemistry 4929, 1989 and Hampel et al., 18 Nucleic Acids Research .299, 1990, and an example of the hepatitis delta virus motif is described by Perrotta and Been, 31 Biochemistry 16, 1992, of the RNAseP motif by Guerrier-Takada et al., 35 Cell 849, 1983, and of the group I intron by Cech et al., U.S. Pat. No. 4,987,071. These specific motifs are not limiting in the invention and those skilled in the art will recognize that all that is important in an enzymatic RNA molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for designing a class of enzymatic cleaving agents which exhibit a high degree of specificity for the RNA of a desired target. The ribozyme molecule is preferably targeted to a highly conserved sequence region of a target such that specific treatment of a disease or condition can be provided with a single ribozyme. Such enzymatic RNA molecules can be delivered exogenously to specific cells as required. In the preferred hammerhead motif the small size (less than 40 nucleotides, preferably between 32 and 36 nucleotides in length) of the molecule allows the cost of treatment to be reduced compared to other ribozyme motifs.

Synthesis of ribozymes greater than 100 nucleotides in length is very difficult using automated methods, and the therapeutic cost of such molecules is prohibitive. Delivery of ribozymes by expression vectors is primarily feasible using only ex vivo treatments. This limits the utility of this approach. In this invention, small ribozyme motifs (e.g., of the hammerhead structure) are used for exogenous delivery. The simple structure of these molecules also increases the ability of the ribozyme to invade targeted regions of the mRNA structure. Thus, unlike the situation when the hammerhead structure is included within longer transcripts, there are no non-ribozyme flanking sequences to interfere with correct folding of the ribozyme structure or with complementary region.

Summary of the Invention

Applicant has devised a method by which the accessibility of any particular target site for a ribozyme can be determined in vitro or in vivo. This assay is important to ensure that time and energy is not expended on developing highly active ribozymes which are unable to locate or bind to a target sequence in vivo because it is later found that the target sequence is inaccessible to the ribozyme. Such inaccessibility may be caused by the target RNA secondary structure, or by protein factors which bind to the target sequence. The assay for such target site accessibility can be performed without the need to form many ribozymes against each potential target site.

In general, the method involves use of an enzyme which is able to recognize a DNA-RNA duplex, and cleave the RNA in that duplex. For example, RNAseH can be used to cleave RNA bound to a DNA molecule. Applicant recognizes that the target site for a ribozyme is an RNA substrate molecule and that an RNA-DNA duplex can be formed with such a target site by provision of suitable complementary DNA. The method involves providing one or more such DNA oligonucleotides or molecules (which may be synthesized quickly and cheaply on a DNA synthesizer), allowing those DNA molecules to contact the target RNA, and determining whether the RNA target is rendered susceptible to cleavage by RNAseH. Such cleavage may be measured by gel electrophoresis of labelled target RNA, or by northern blotting, as well as by other methodology well known in the art.

The method of this invention allows DNA probes of various sizes to be chosen such that they approximate the size and shape of the ribozyme binding site so that accessibility of the entire ribozyme structure can be evaluated. In addition, since many eukaryotic cells contain endogenous RNAseH, it is possible to use the method to evaluate target site accessibility in whole living cells by delivering the DNA oligonucleotides to those cells under conditions in which endogenous RNAseH will cleave any RNA-DNA duplexes formed in the cell.

Thus, the invention features a method for determining RNA target site accessibility to a ribozyme by providing a DNA oligonucleotide complementary to the RNA target site and contacting that DNA oligonucleotide with the RNA target in the presence of a DNA-RNA specific cleaving agent, such as RNAseH, so that the RNAseH will cleave the RNA target when the DNA and RNA form a duplex. The occurrence of cleavage is detected by any standard methodology, e.g., northern blot or gel electrophoresis. Those DNA oligonucleotides which provide a detectable level of cleavage indicate that the complementary RNA target site is accessible to a ribozyme. Ribozymes to these target sites can then be synthesized, using standard methodology, and checked to determined that the RNA target site is truly accessible to a ribozyme.

By "target site" is meant a sequence within a target RNA that is "targeted" for cleavage: (i) by a ribozyme which contains sequences within its substrate-binding domain that are complementary to the target sequence, or (ii) by a DNA/RNA cleaving agent, such as RNAseH, following the binding of a complementary DNA oligonucleotide to the target sequence.

By "substrate-binding domain" is meant sequences within a ribozyme which are intended to bring ribozyme and target RNA together through complementary base-pairing interactions; e.g., ribozyme sequences within stems I and III of a standard hammerhead ribozyme make up the substrate-binding domain (see FIG. 7).

By "DNA oligonucleotide" is meant a short sequence of DNA; in this application, the sequence is in the range of 7–20 nucleotides, and preferably in the range of 9–13 nucleotides.

By "RNAseH" is meant an endoribonuclease that degrades the RNA portion of RNA-DNA hybrid duplexes. RNAseH is found in many organisms; E. coli RNAseH is available from many commercial sources.

By "detectable level of cleavage" is meant cleavage of target RNA (and formation of cleaved product RNAs) to an extent sufficient to discern cleavage products above the background of RNAs produced by random degradation of the target RNA. Production of cleavage products from 1–5% of the target RNA is sufficient to detect above the background for most methods of detection.

In preferred embodiments, the DNA oligonucleotides are between 9–15 bases in length, and completely complementary to the target site.

Other features and advantages of the invention will be apparent from the following description of the preferred embodiments thereof, and from the claims.

DESCRIPTION OF THE PREFERRED EMBODIMENT

The drawings will first briefly be described.

Drawings

Figure 1B:
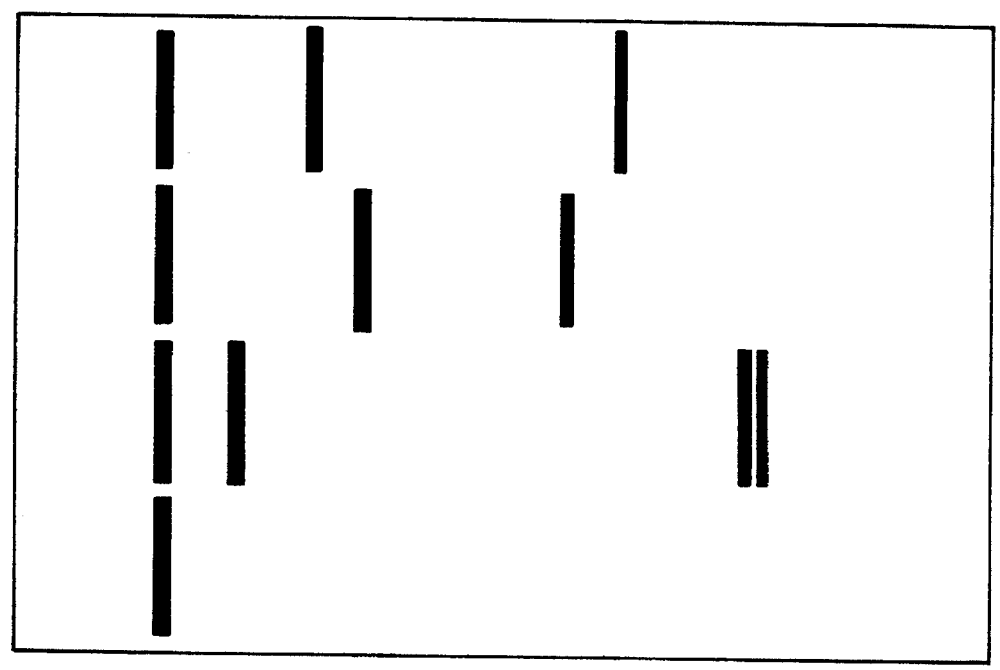
Figure 1A:
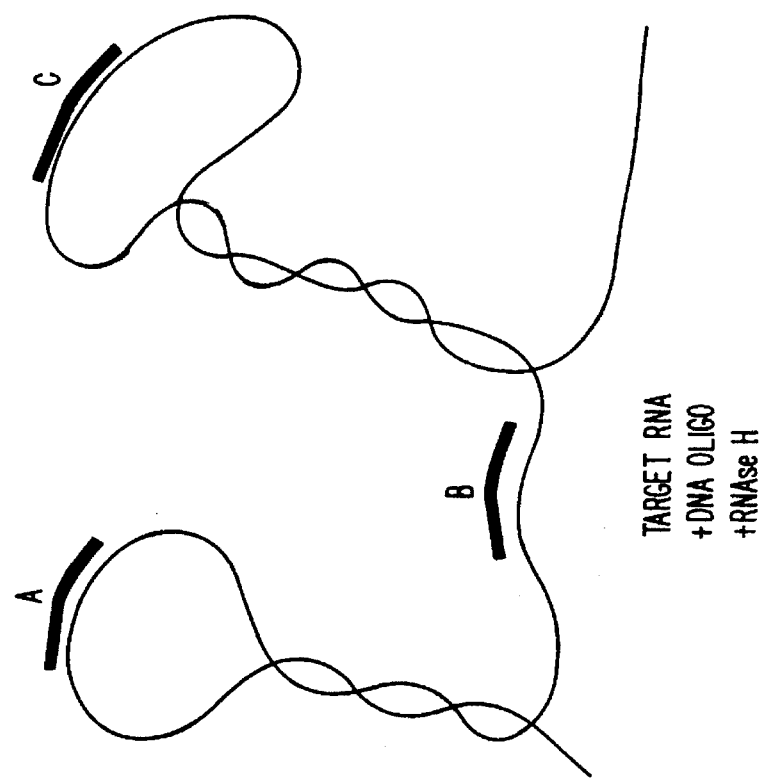

FIGS. 1A and 1B are a schematic representation of an RNAseH accessibility assay. Specifically, FIG. 1A is a diagram of complementary DNA oligonucleotides bound to accessible sites on the target RNA. Complementary DNA oligonucleotides are represented by broad lines labelled A, B, and C. Target RNA is represented by the thin, twisted line. FIG. 1B is a schematic of a gel separation of uncut target RNA from a cleaved target RNA. Detection of target RNA is either by autoradiography of body-labelled target RNA, by northern blotting with labelled target cDNA or by RNAse protection with labelled RNA. The bands in each lane represent uncut target RNA. The remaining bands in each lane represent the cleaved products.

Figure 2:
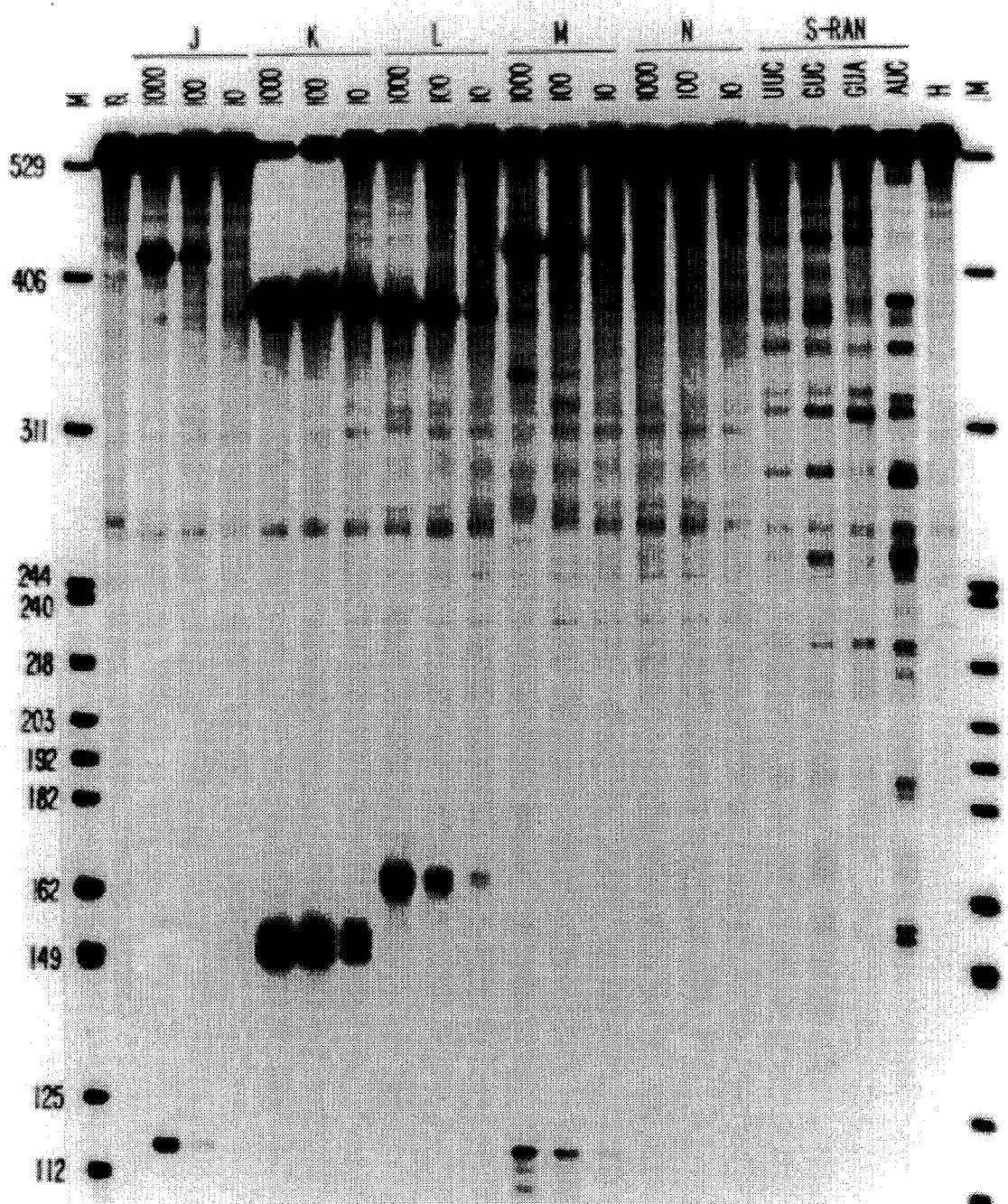

FIG. 2 is a copy of an autoradiogram of an RNAseH assay performed on in vitro transcribed target RNA using five probes to a portion of the HSV ICP27 mRNA. Probes labelled J, K, L, M, and N respectively represent five 13-mer DNA oligonucleotides complementary to five different sites on ICP27 (see Table 2). The end lanes labelled M are DNA size markers (DNA sizes are indicated at the left of the figure). Lanes labelled § and H represent target RNA immediately after transcription (§) or after incubation with RNAseH but without a DNA oligonucleotide (H). Lanes marked 1000, 100 and 10 represent digestion by RNAseH in the presence of 1000 nM, 100 nM and 10 nM respectively of DNA probe. Lanes marked S-RAN: UUC, GUC, GUA and AUC represent digestion of target RNA by RNAseH in the presence of 10 μM of the semi-random DNA oligonucleotides containing 12-nucleotides total with the middle three comprising sequences complementary to UUC, GUC, GUA and AUC, respectively.

TABLE 2

Sequence and position of ICP27 oligos used in RNAse H assays.

| Site | Oligo Name | Position | Sequence |
|------|------------|----------|----------|
| D | GDCr12 | 142 | CGCCATGACCGG |
| E | GECr13 | 279 | TCGTCCGACGAGG |
| E1 | ICP27E1 | 330 | GCGTCGAGTATCG |
| J | GJCr13 | 1072 | CCAGGAGACCCGT |
| K | GKCr13 | 1108 | GCGATAGAGGCTC |
| K2 | ICP27k2 | 1110 | AAGTGCGATAGAG |
| K7 | ICP27K7 | 1109 | TGCGATA |
| K9 | ICP27K9 | 1108 | GTGCGATAG |
| K11 | ICP27K11 | 1107 | AGTGCGATAGA |
| L | GLCR13 | 1134 | ACTGGAGAAAGGC |
| M | GMCR13 | 1386 | CGCCGCGAACACA |
| N | GNCR13 | 1462 | ACGCTCGACGCGG |
| T | GTCr13 | 1979 | GGCGTTGAGGCAG |
| U | 271U | 252 | CTGTCCGATTCCA |
| — | AUC/S-RAN | ? | NNNNGAUNNNN |
| — | GUA/S-RAN | ? | NNNNUACNNNN |
| — | GUC/S-RAN | ? | NNNNGACNNNN |
| — | UUC/S-RAN | ? | NNNNGAANNNN |

Position:
the nucleotide position of the target sequence in ICP27. The transcription start is position 1. The actual positions of RNAse H cleavage promoted by the semirandom probes has not been determined.
Sequence:
The sequence of DNA oligonucleotides used as RNAse H probes to accessibility at the given site. The probe sequences are complementary to the target sequence. N represents a population of molecules with all four nucleotides (A, C, G, & U) represented.

Figure 3:
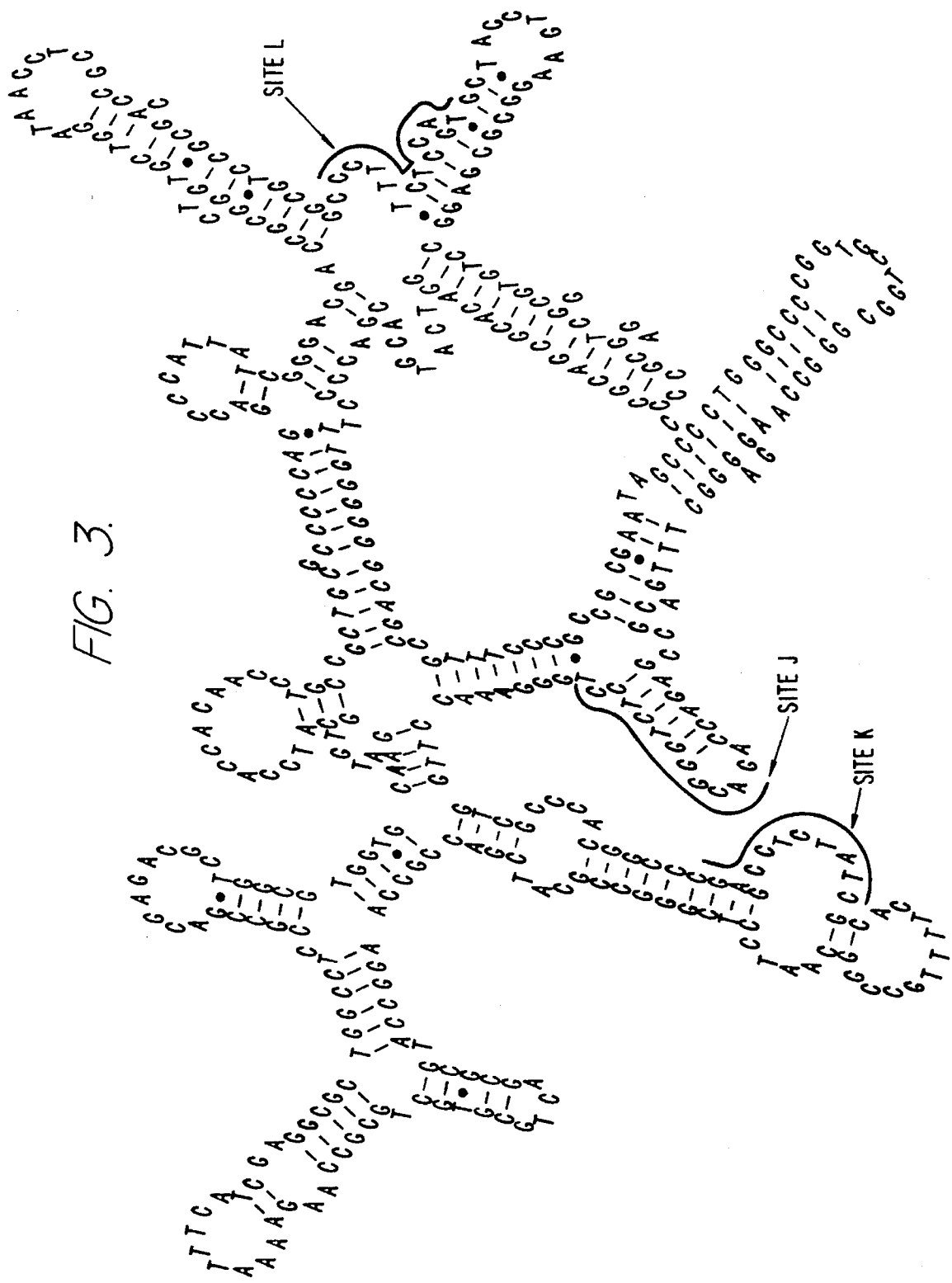

FIG. 3 is a computer generated folding pattern of the sequence of HSV ICP27 from nucleotides 952–1376. Three of the sites that were targeted for cleavage in FIG. 2 are indicated by broad lines and labels (sites J, K and L).

Figure 4:
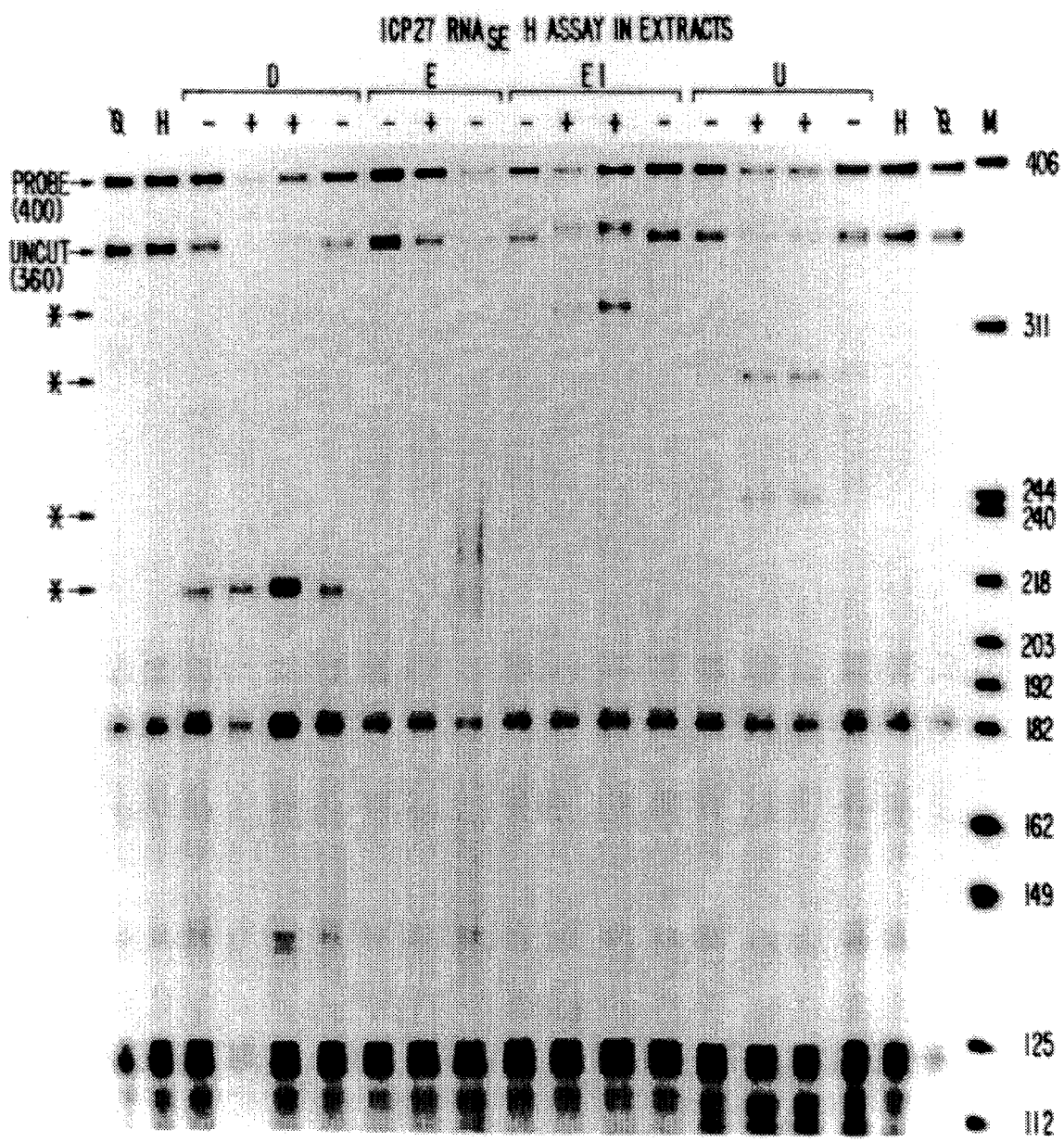

FIG. 4 is a copy of an autoradiogram of an RNAseH assay performed on HSV ICP27 mRNA contained in a cellular extract, using four DNA oligonucleotide probes. Target RNA was produced by infection of Vero cells with Herpes Simplex Virus (HSV). Cell extracts were separated into nuclear, cytoplasmic and membrane fractions. ICP27 RNA in the cytoplasmic fraction was probed for accessibility to RNAseH cleavage in the presence of 15 µM DNA oligonucleotides complementary to site D, E, E1 or U. Cleaved and full-length target RNA was detected by RNAse protection assay using a 400 nucleotide antisense RNA. Full-length message was detected as a 360 nucleotide band, while cleaved message was detected as bands in the 200–330 nucleotide size range. Each site was probed twice without added RNAseH (labelled "–") and twice in the presence of RNAseH (labelled "+"). Cleavage products in the "–" lane for site D confirms the presence of endogenous RNAseH in the extracts.

Figure 5:
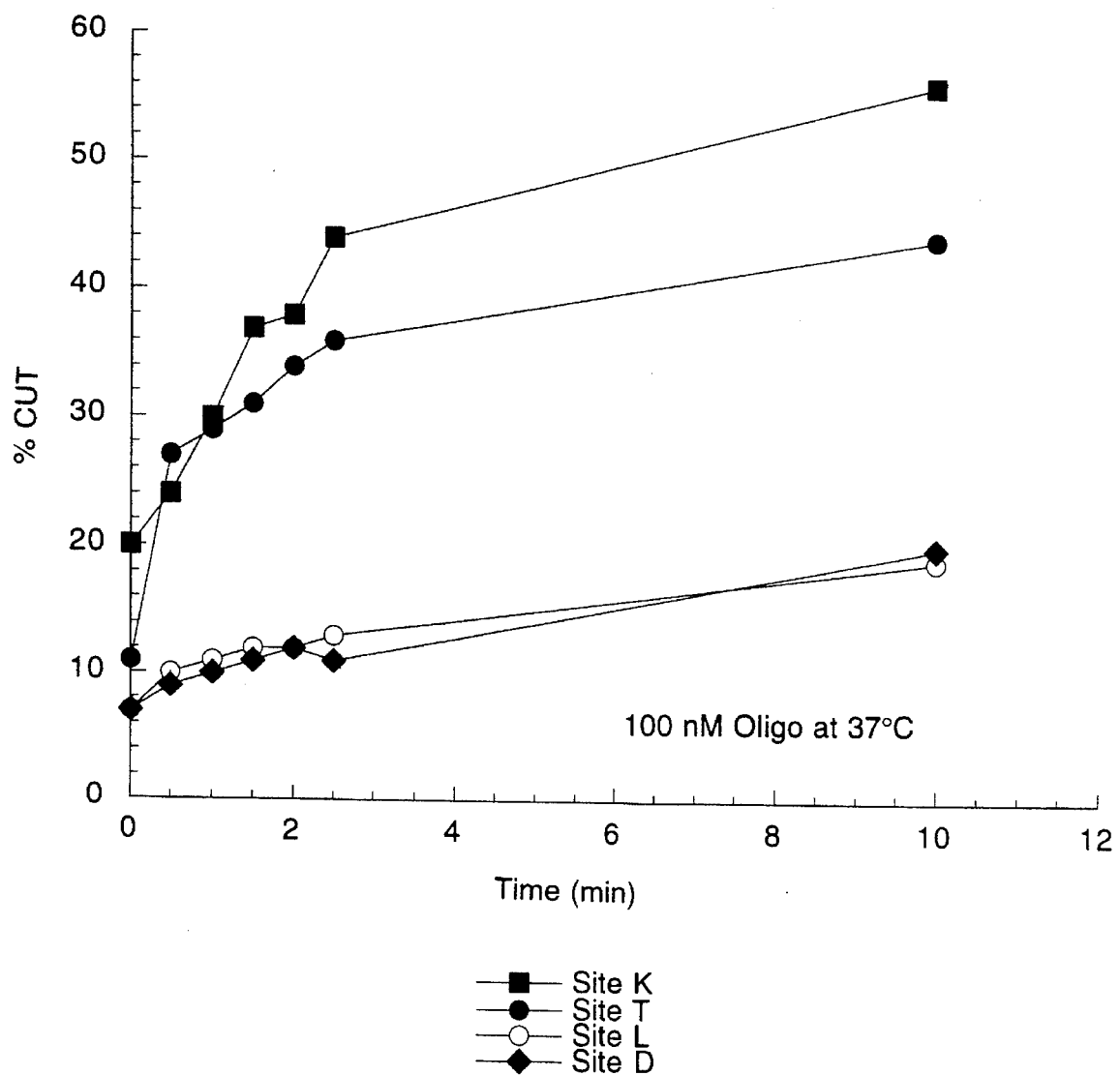

FIG. 5 is a graph showing quantitation of RNAseH cleavage rates at different sites on HSV ICP27. Sites K and T show efficient levels of cleavage at this DNA probe concentration; sites D and L show only low levels of cleavage.

Figure 6:
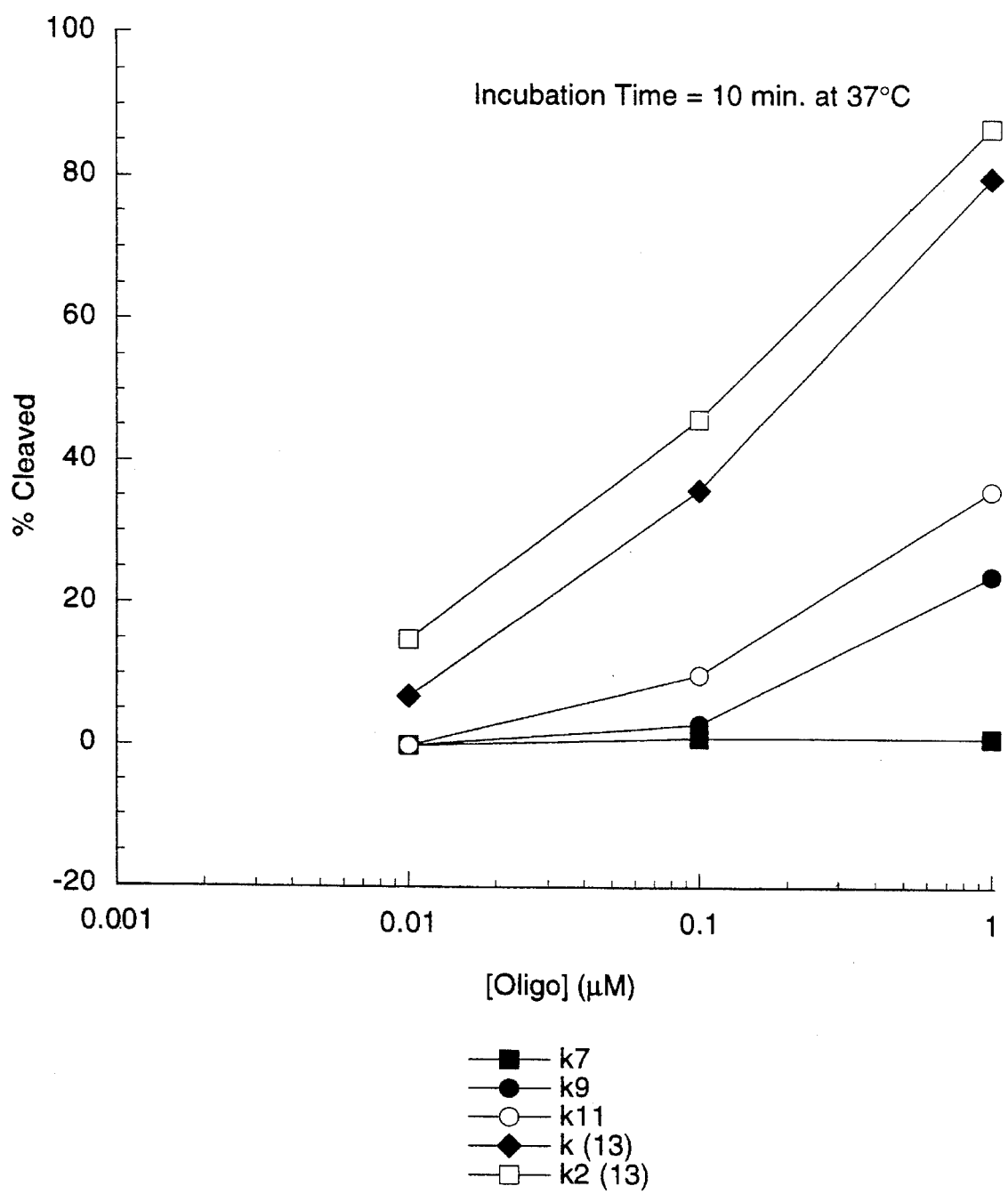

FIG. 6 is a graph illustrating the effect of DNA probe length on RNAseH cleavage activity at an accessible site (K) in ICP27 target RNA. A plot of cleavage activity (% target RNA cleaved) as a function of DNA probe concentration for DNA probes of length 7, 9, 11 and 13 nucleotides is shown. The 7 nucleotide probe shows no activity even at 1 µm concentrations, suggesting that probe lengths greater than 7 nucleotides are preferred.

Figure 7:
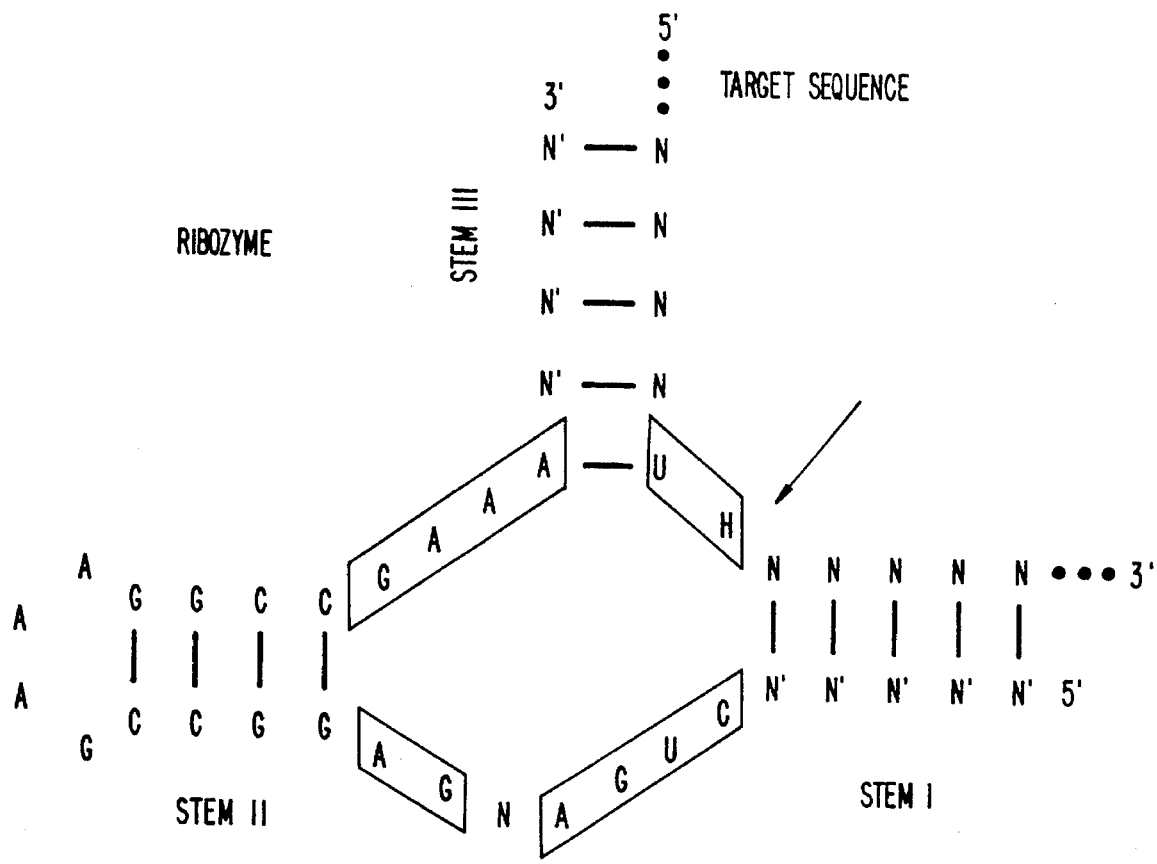

FIG. 7, is a diagrammatic representations of hammerhead ribozyme, showing the secondary structure of the ribozyme bound to its target sequence. Boxed nucleotides are required for activity. Bars indicate Watson-Crick base-pairs. H represents nucleotides C, A, or U. arrows shows location of cleavage site in the target sequence.

Figure 8:
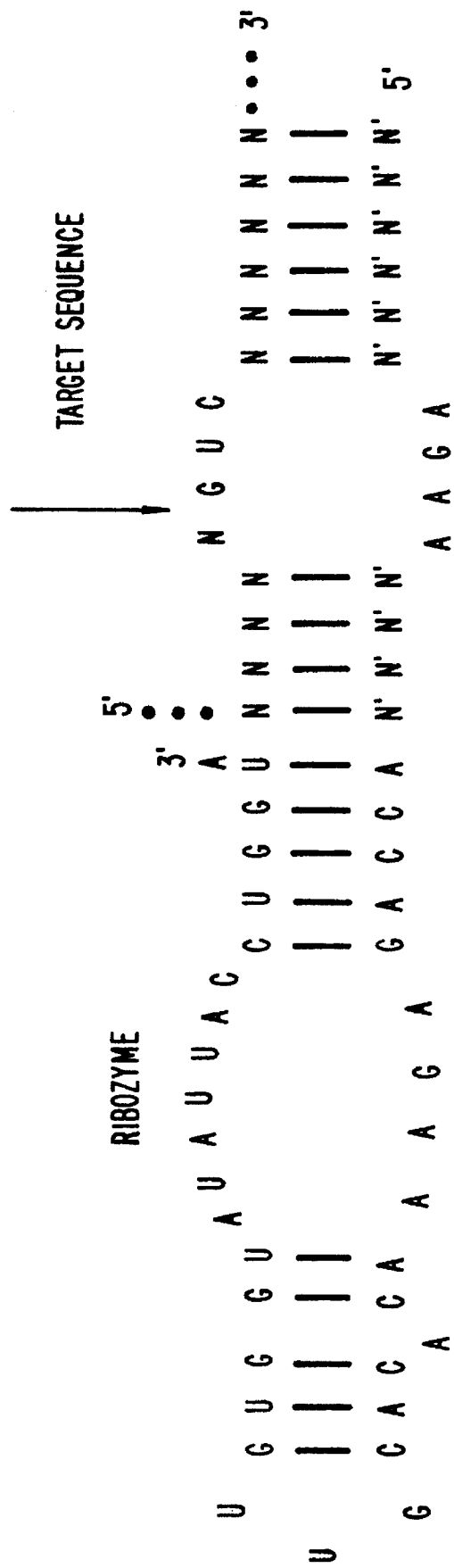

FIG. 8 is a diagrammatic representation of a hairpin ribozyme, showing the proposed secondary structure of the hairpin ribozyme bound to its target sequence. Bars indicate Watson-Crick base-pairing. N and N' are any nucleotide pairs that form Watson-Crick base-pairs. Arrow shows location of cleavage site in the target sequence.

Figure 9:
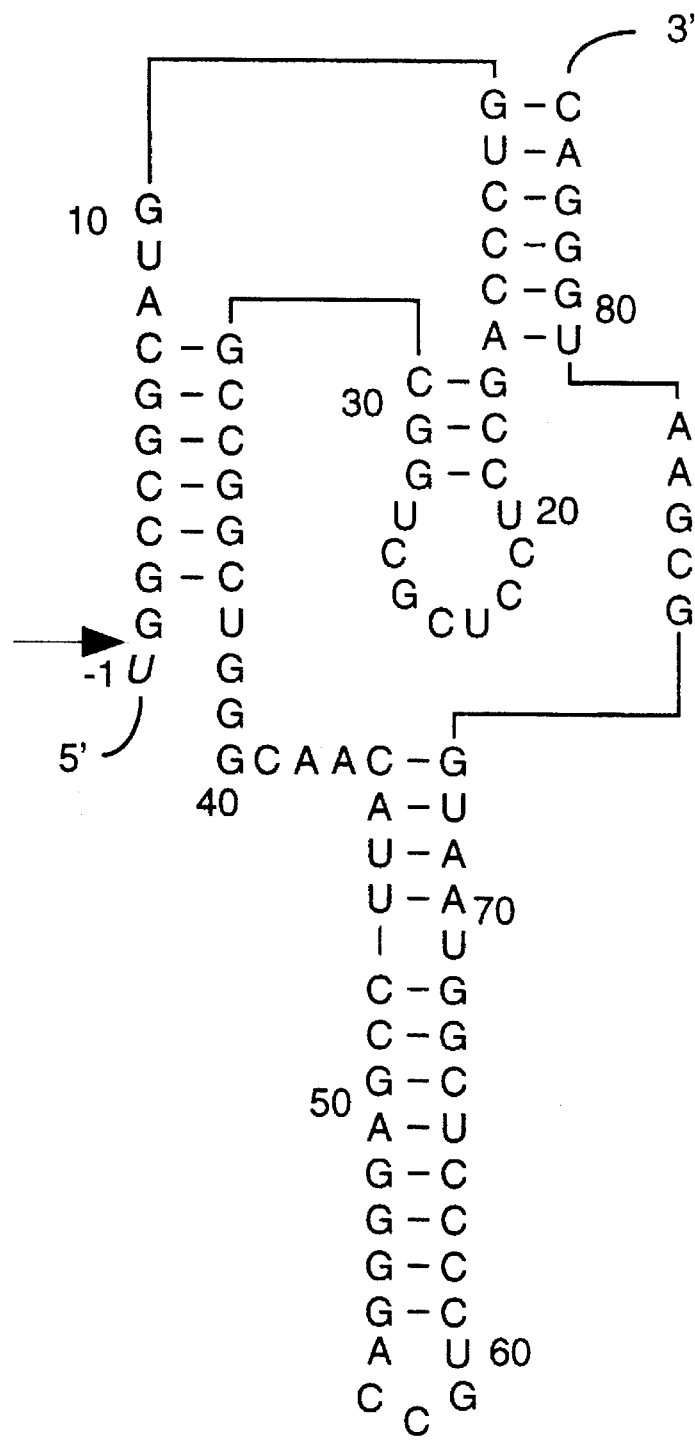

FIG. 9 is a diagrammatic representation of a Hepatitis Delta Virus (HDV) ribozyme showing the proposed secondary structure of the catalytic portion of the HDV genomic strand. Numbering indicates nucleotide position relative to the cleavage site. Arrow shows location of cleavage site. Structure from Perrotta and Been (1991) *Nature* 350:434.

Method

The method of the invention is generally described above. Examples of methods of the invention are provided below, and in the Figures discussed above, which are not limiting to this invention. Those of ordinary skill in the art will recognize that many equivalents to such methods can be used.

The assay of this invention does not provide a final test of target site accessibility, but rather provides a preliminary test. A number of factors may cause the test to distort the picture of which sites are accessible and which are not. For example, the enzyme used, e.g., RNAseH, may cut the target RNA at a site that is only partially bound by a DNA oligonucleotide. Such a site may thus be only partially susceptible to RNAseH cleavage, and not accessible at all to a ribozyme. The occurrence of such an erroneous false positive result can be reduced by testing each RNA target site with a set of overlapping DNA oligonucleotides. In addition, a DNA oligonucleotide does not have exactly the same binding affinity as an RNA oligonucleotide, so that a site that is inaccessible to a DNA probe still may be accessible to an RNA probe, or vice versa. For the most part such differences are small, and false negative results are rare. Again, misguidance by the occurrence of such false results can be avoided by use of several different DNA oligonucleotides for each test site.

The DNA oligonucleotide used may completely span the ribozyme binding site in just one helix (i.e., with no base mismatches, bulges or loops). In contrast, an equivalent ribozyme binding at the same site may have two binding regions split by a core sequence, e.g., this is the case for a hammerhead ribozyme. The presence of such a central core may reduce the binding affinity of the ribozyme compared to a DNA oligonucleotide by as much as 7.0 kcal/mole; thus, a DNA oligonucleotide may bind many times more strongly than the equivalent ribozyme. The possibility of this discrepancy can be reduced by use of short DNA oligonucleotides (9–13 bases). Since short oligonucleotides will not necessarily bind to the same site as the ribozyme, a number of shorter overlapping DNA should be used in each set of experiments.

In general, the strategy involves the formation of DNA oligonucleotides complementary to any number of selected RNA target sites. The target RNA can be transcribed in vitro using labelled nucleotide triphosphates, and added directly to an RNAseH assay mixture. The target RNA is preferably not purified in order to keep its configuration as close as possible to that in a natural in vivo environment. The DNA oligonucleotides are mixed in various concentrations with an excess of RNAseH and the labelled target RNA and incubated at 37° C. Samples are removed at various times and loaded onto sequencing gels. The most useful RNA target sites are those that show the largest extent of cleavage in the shortest amount of time.

The RNAseH experiments can also be performed as described above, except that the target RNA need not be labelled, and can be provided within a cell extract. Northern blotting (or other means, e.g., RNAse protection) of the RNA can then be used to detect cleavage of the RNA.

In one type of experiment, in vitro transcribed, body-labelled target RNA is digested by addition of high concentrations of RNAseH in the presence of varying concentrations of 9–15 mer DNA oligonucleotides complementary to specific sites on the target. The high concentration of RNAseH reduces the probability that cleavage by RNAseH will be the rate-limiting step in the reaction. Thus, differences in RNA cleavage rates (and extents) are interpreted to represent differences in rates (and extents) of association between the DNA oligonucleotides and their respective sites on the target RNA. Sites which are accessible to cleavage by RNAseH are more likely to be targetable by ribozymes.

In a further experiment, we have employed semi-random DNA oligonucleotides as RNAseH probes of target RNA accessibility. The semi-random probes are of the form, NXYZN, where N represents a randomized position (i.e., A, C, G, or T; or each N is individually between 0 and 12 nucleotides, and the oligonucleotide contains at least 8–12 nucleotides) and XYZ represents a specific sequence complementary to one of the preferred ribozyme cleavage sequences (e.g., GUC, GUA, CUC, CUA). Probing with fully randomized DNA provides unsatisfactory results; cleavage of the target RNA occurs only at high probe concentrations and without the formation of discernable bands. The semi-random probes described above permit a large number of potential target sites to be evaluated from a single reaction. The number of different sequences represented in the semi-random probe, however, is only a fraction ($4^{-3}$ or 1.6%) of sequences present in a completely random probe. This has the advantage of increasing the concentration of any given sequence while the number of bands to be interpreted is kept to a manageable number.

EXAMPLES

The following are examples of use of the invention. These examples are illustrated in the figures, and are not limiting in this invention, Those in the art will recognize that many equivalent procedures can be used within the scope of the invention.

EXAMPLE 1: RNAseH in vitro

The following reagents were used:

5X buffer:

100 mM Tris pH 7.9

500 mM KCl 50 mM $MgCl_2$ 0.5 mM EDTA 0.5 mM DTT

RNAseH:

Obtained from Bethesda Research Labs. (BRL) 2.5 U/μl

Formamide dye stop:

95% Formamide 20 mM EDTA 0.1% bromophenol blue 0.1% xylene cyanol

DNA oligonucleotide (typically 13 nucleotide long) at a 10X concentration of 10, 1, and 0.1 μM.

The method involved the following steps:

1. Dilute a standard transcription reaction (including the target RNA formed by transcription in a cell lysate or in a test tube) to the appropriate counts per minute (cpm) per μl to a 10X concentration;

| 2. Set up the reaction mix: | (typical reaction) |
|---|---|
| 5x Buffer | 2.0 μl |
| Body labelled Target RNA 50,000 (cpm/λ) | 1.0 μl |
| RNAseH (2.5 μ/λ) | 0.32 μl |
| $H_2O$ | 5.68 μl |
| | 9.0 μl |

3. Prewarm reaction mix to 37° C., then add 1 μl of DNA oligonucleotide. Allow to incubate at 37° C. for 10 minutes, then add 5 μl of formamide stop solution. Brief spin to remove condensation from the tubes wall, then heat at a minimum of 90° C. for 3' before loading onto a denaturing acrylamide gel. EXAMPLE 2: RNAseH in Cell Extracts The following reagents were used:

5X buffer:

100 mM Tris pH 7.9

500 mM KCl 50 mMMgCl$_2$ 0.5 mM EDTA 0.5 mM DTT

RNAseH:

BRL 2.5 U/μl

Cell lysis buffer:

4 M guanidine thiocyanate 0.5% sarcosyl 25 mM sodium citrate pH 7.4

Formamide dye stop:

95% Formamide 20 mM EDTA 0.1% bromophenol blue 0.1% xylene cyanol

RNAse Solution:

0.4 M NaCl 10 mM $MgCl_2$

20 U/ml RNAseA (United States Biochemical Co. Ohio; USB)

2 U/ml RNAse T1 (USB)

4 U/ml DNAse 1, RNAse free (USB)

20% SDS

Proteinase K: 20 mg/ml

Phenol: chloroform: isoamyl alcohol 25:25:1

Isopropanol tRNA: 2 μg/μl

DNA oligonucleotide (typically 13 nucleotide long) at a 10X concentration of 150 μM.

After preparing a cell lysate (from a cell including a target RNA) using standard procedures the method involved the following steps:

| 1. In a 0.5 ml tube add: | |
|---|---|
| 5x buffer | 3 μl |
| cell lysate | 10 μl |
| RNAseH | 0.3 μl |
| $H_2O$ | 1.68 μl |
| | 14 μl |

2. Prewarm to 37° C. and add 1 μof 10X stock of DNA oligonucleotide, incubate at 37° C. for 10 minutes and stop the reaction by adding 40 μof lysis buffer.

3. Add 5 μof labelled RNAse protection probe RNA (200,000 cpm/λ), overlay with 25 μof mineral oil and hybridize overnight at 55° C.

4. Transfer to a 1.5 ml tube containing 500 μl of RNAse solution and incubate at 37° C. for 30 minutes.

5. Add 10 μof 20% SDS and 10 μof 20 mg/ml proteinase K, incubate at 37° C. for 30 minutes.

6. Extract once with 500 μl of 25:25:1 mixture of phenol: chloroform: isoamyl alcohol, brief vortex and transfer the aqueous phase to a fresh 1.5 ml tube containing 500 μl of isopropyl alcohol with tRNA carrier.

7. Pellet at room temperature (about 20° C.) for 8 minutes.

8. Resuspend in 10 μl of formamide dye stop.

9. Heat above 90° C. for over 3 minutes and load onto a denaturing acrylamide gel.

Results of the above two examples are shown in the Figures. These results were obtained using the standard procedures described above and other standard protocols well known in the art.

Other embodiments are within the following claims.

I claim:

1. A method for determining ribozyme target site accessibility and synthesis of a ribozyme, comprising the step of: contacting a DNA oligonucleotide complementary to the target RNA with said target RNA in the presence of RNaseH under RNA cleaving conditions; wherein cleavage by RNaseH indicates accessibility of said target RNA; and synthesizing a ribozyme to a said accessible target RNA.

2. The method of claim 1 wherein cleavage of said RNA is detected by gel electrophoresis, northern blot analysis, or RNAse protection assays.

3. The method of claim 1, wherein a plurality of said DNA oligonucleotides is provided.

4. The method of claim 3 wherein said plurality of DNA oligonuceotides are of the form N'XYZN where each N and N' is independently any nucleotide sequence from 0–12 nucleotides in length and XYZ is a specific base sequence, and each said oligonucleotide comprises at least 8 nucleoides.

5. The method of claim 1 wherein said DNA oligonucleotides consists of from 8 to 15 bases.

6. The method of claim 5, wherein said DNA oligonucleotide consists of from 10 to 15 bases.

7. A method for identifying a region of RNA accessible to cleavage by a ribozyme, comprising the step of:

contacting a plurality of DNA oligonucleotides complementary to the RNA to be cleaved in the presence of RNaseH adapted to cleave the RNA of an RNA-DNA duplex under RNA cleaving conditions, wherein said DNA oligonucleotides are selected to hybridize to the RNA at a plurality of regions; and detecting cleavage of the RNA as an indicator of the most accessible region of the RNA to a ribozyme.

8. The method of claim 7 wherein said detecting is by gel electrophoresis.

9. The method of claim 7 wherein said DNA oligonucleotides are of the form NGAN, NUAN, or NXYZN where each N is any sequence of length 0–12 nucleotides, and XYZ is selected from the group consisting of GAA, GAC, GAG, GAU, UAA, UAC, UAG and UAU and the oligonucleotide has a length of at least 8 nucleotides.

10. The method of claim 7 wherein said DNA oligonucleotides are single-stranded fragments of a gene encoding the target RNA.

11. The method of claim 10 wherein said DNA oligonucleotides are obtained by asymmetric amplification followed by fragmentation by use of thiophosphate incorporation followed by peroxide degradation.

12. The method of claim 7 wherein said detecting is by RNAse protection.

13. The method of claim 7 wherein said detecting is by northern blot analysis.

14. The method of claim 10 wherein said DNA oligonucleotides are obtained by asymmetric amplification followed by fragmentation by use of chemical cleavage.

15. The method of claim 10 wherein said DNA oligonucleotides are obtained by asymmetric amplification followed by fragmentation by use of DNAseI digestion.

* * * * *

UNITED STATES PATENT AND TRADEMARK OFFICE
CERTIFICATE OF CORRECTION

PATENT NO. : 5,525,468
DATED : June 11, 1996
INVENTOR(S) : James A. McSwiggen

It is certified that error appears in the above-indentified patent and that said Letters Patent is hereby corrected as shown below:

Column 4, line 41: please add --(-- before M1

Column 5, line 16: please delete "Geriach" and add --Gerlach--

Column 6, line 7: please delete "." before 299

Column 8, line 31: please add a space between RNAby

Column 12, lines 42-49: please add --1 -- before of

Signed and Sealed this

Tenth Day of June, 1997

*Attest:*

BRUCE LEHMAN

*Attesting Officer*     Commissioner of Patents and Trademarks

SEQUENCE LISTING ( 1 ) GENERAL INFORMATION:

( i i i ) NUMBER OF SEQUENCES: 22

( 2 ) INFORMATION FOR SEQ ID NO: 1:

( i ) SEQUENCE CHARACTERISTICS:
( A ) LENGTH: 12
( B ) TYPE: nucleic acid
( C ) STRANDEDNESS: single
( D ) TOPOLOGY: linear ( i i ) SEQUENCE DESCRIPTION: SEQ ID NO: 1:

CGCCATGACC GG 12

( 2 ) INFORMATION FOR SEQ ID NO: 2:

( i ) SEQUENCE CHARACTERISTICS:
( A ) LENGTH: 13
( B ) TYPE: nucleic acid
( C ) STRANDEDNESS: single
( D ) TOPOLOGY: linear ( i i ) SEQUENCE DESCRIPTION: SEQ ID NO: 2:

TCGTCCGACG AGG 13

( 2 ) INFORMATION FOR SEQ ID NO: 3:

( i ) SEQUENCE CHARACTERISTICS:
( A ) LENGTH: 13
( B ) TYPE: nucleic acid
( C ) STRANDEDNESS: single
( D ) TOPOLOGY: linear ( i i ) SEQUENCE DESCRIPTION: SEQ ID NO: 3:

GCGTCGAGTA TCG 13

( 2 ) INFORMATION FOR SEQ ID NO: 4:

( i ) SEQUENCE CHARACTERISTICS:
( A ) LENGTH: 13
( B ) TYPE: nucleic acid
( C ) STRANDEDNESS: single
( D ) TOPOLOGY: linear ( i i ) SEQUENCE DESCRIPTION: SEQ ID NO: 4:

CCAGGAGACC CGT 13

( 2 ) INFORMATION FOR SEQ ID NO: 5:

( i ) SEQUENCE CHARACTERISTICS:
( A ) LENGTH: 13
( B ) TYPE: nucleic acid
( C ) STRANDEDNESS: single
( D ) TOPOLOGY: linear ( i i ) SEQUENCE DESCRIPTION: SEQ ID NO: 5:

GCGATAGAGG CTC 13

( 2 ) INFORMATION FOR SEQ ID NO: 6:

( i ) SEQUENCE CHARACTERISTICS:
( A ) LENGTH: 13
( B ) TYPE: nucleic acid
( C ) STRANDEDNESS: single
( D ) TOPOLOGY: linear ( i i ) SEQUENCE DESCRIPTION: SEQ ID NO: 6:

AAGTGCGATA GAG                                                                    13

( 2 ) INFORMATION FOR SEQ ID NO: 7:

( i ) SEQUENCE CHARACTERISTICS:
        ( A ) LENGTH: 7
        ( B ) TYPE: nucleic acid
        ( C ) STRANDEDNESS: single
        ( D ) TOPOLOGY: linear ( i i ) SEQUENCE DESCRIPTION: SEQ ID NO: 7:

TGCGATA                                                                            7

( 2 ) INFORMATION FOR SEQ ID NO: 8:

( i ) SEQUENCE CHARACTERISTICS:
        ( A ) LENGTH: 9
        ( B ) TYPE: nucleic acid
        ( C ) STRANDEDNESS: single
        ( D ) TOPOLOGY: linear ( i i ) SEQUENCE DESCRIPTION: SEQ ID NO: 8:

GTGCGATAG                                                                          9

( 2 ) INFORMATION FOR SEQ ID NO: 9:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i i ) SEQUENCE DESCRIPTION: SEQ ID NO: 9:

AGTGCGATAG A                                                                       11

( 2 ) INFORMATION FOR SEQ ID NO: 10:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) SEQUENCE DESCRIPTION: SEQ ID NO: 10:

ACTGGAGAAA GGC                                                                    13

( 2 ) INFORMATION FOR SEQ ID NO: 11:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) SEQUENCE DESCRIPTION: SEQ ID NO: 11:

CGCCGCGAAC ACA                                                                    13

( 2 ) INFORMATION FOR SEQ ID NO: 12:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) SEQUENCE DESCRIPTION: SEQ ID NO: 12:

ACGCTCGACG CGG					13

( 2 ) INFORMATION FOR SEQ ID NO: 13:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) SEQUENCE DESCRIPTION: SEQ ID NO: 13:

GGCGTTGAGG CAG					13

( 2 ) INFORMATION FOR SEQ ID NO: 14:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) SEQUENCE DESCRIPTION: SEQ ID NO: 14:

CTGTCCGATT CCA					13

( 2 ) INFORMATION FOR SEQ ID NO: 15:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) SEQUENCE DESCRIPTION: SEQ ID NO: 15:

ACGGGUCUCC UGG					13

( 2 ) INFORMATION FOR SEQ ID NO: 16:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) SEQUENCE DESCRIPTION: SEQ ID NO: 16:

GAGCCUCUAU CGC					13

( 2 ) INFORMATION FOR SEQ ID NO: 17:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) SEQUENCE DESCRIPTION: SEQ ID NO: 17:

GCCUUUCUCC AGU					13

( 2 ) INFORMATION FOR SEQ ID NO: 18:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"
            stands for any base.

"H"represents nucleotide C, A, or U.

(i i) SEQUENCE DESCRIPTION: SEQ ID NO: 18:

NNNNUHNNNN N    11

(2) INFORMATION FOR SEQ ID NO: 19:

(i) SEQUENCE CHARACTERISTICS:
    (A) LENGTH: 32
    (B) TYPE: nucleic acid
    (C) STRANDEDNESS: single
    (D) TOPOLOGY: linear (i x) FEATURE:
    (D) OTHER INFORMATION: The letter "N" stands for any base.

(i i) SEQUENCE DESCRIPTION: SEQ ID NO: 19:

NNNNCUGAN GAGGCCGAAA GGCCGAAANN NN    32

(2) INFORMATION FOR SEQ ID NO: 20:

(i) SEQUENCE CHARACTERISTICS:
    (A) LENGTH: 14
    (B) TYPE: nucleic acid
    (C) STRANDEDNESS: single
    (D) TOPOLOGY: linear (i x) FEATURE:
    (D) OTHER INFORMATION: The letter "N" stands for any base.

(i i) SEQUENCE DESCRIPTION: SEQ ID NO: 20:

NNNNNGUCNN NNNN    14

(2) INFORMATION FOR SEQ ID NO: 21:

(i) SEQUENCE CHARACTERISTICS:
    (A) LENGTH: 50
    (B) TYPE: nucleic acid
    (C) STRANDEDNESS: single
    (D) TOPOLOGY: linear (i x) FEATURE:
    (D) OTHER INFORMATION: The letter "N" stands for any base.

(i i) SEQUENCE DESCRIPTION: SEQ ID NO: 21:

NNNNNNAGAA NNNNACCAGA GAAACACACG UUGUGGUAUA UUACCUGGUA    50

(2) INFORMATION FOR SEQ ID NO: 22:

(i) SEQUENCE CHARACTERISTICS:
    (A) LENGTH: 85
    (B) TYPE: nucleic acid
    (C) STRANDEDNESS: single
    (D) TOPOLOGY: linear (i i) SEQUENCE DESCRIPTION: SEQ ID NO: 22:

UGGCCGGCAU GGUCCCAGCC UCCUCGCUGG CGCCGGCUGG GCAACAUUCC    50

GAGGGGACCG UCCCCUCGGU AAUGGCGAAU GGGAC    85